United States Patent [19]

Utsumi et al.

[11] Patent Number: 5,331,948
[45] Date of Patent: Jul. 26, 1994

[54] TIP ARTICULATION MECHANISM FOR ENDOSCOPES

[75] Inventors: Atsushi Utsumi; Masahiro Miura, both of Itami, Japan

[73] Assignee: Mitsubishi Cable Industries, Ltd., Amagasaki, Japan

[21] Appl. No.: 985,658

[22] Filed: Dec. 7, 1992

[30] Foreign Application Priority Data

Dec. 17, 1991 [JP] Japan .................................. 3-353604

[51] Int. Cl.[5] .............................................. H01B 1/00
[52] U.S. Cl. .......................................... 128/4; 604/95
[58] Field of Search ........................ 128/4, 6; 604/95

[56] References Cited

U.S. PATENT DOCUMENTS

| | | | |
|---|---|---|---|
| 4,037,324 | 7/1977 | Andreasen | 32/14 A |
| 4,271,845 | 6/1981 | Chikashige et al. | 128/4 X |
| 4,483,326 | 11/1984 | Yamaka et al. | 128/4 |
| 4,742,817 | 5/1988 | Kawashima et al. | 128/4 |
| 4,982,727 | 1/1991 | Sato | 128/4 |
| 5,002,041 | 3/1991 | Chikama | 128/4 |
| 5,025,804 | 6/1991 | Kondo | 128/4 |
| 5,031,510 | 7/1991 | Krauter | 128/4 X |
| 5,168,864 | 12/1992 | Shockey | 128/4 |
| 5,176,126 | 1/1993 | Chikama | 128/4 |
| 5,181,668 | 1/1993 | Tsuji et al. | 242/54 R |

FOREIGN PATENT DOCUMENTS 3819123  12/1989  Fed. Rep. of Germany .......... 128/4

*Primary Examiner*—Richard J. Apley
*Assistant Examiner*—Beverly A. Meindl
*Attorney, Agent, or Firm*—Armstrong, Westerman, Hattori, McLeland & Naughton

[57] ABSTRACT

A pulling wire for tip articulation mechanism of endoscope is fitted with an overload preventing spring in the middle thereof. This spring is arranged to stretch upon more than a certain amount of tension. Elongation of the overload preventing spring absorbs any excessive tension which is exerted upon the pulling wire as a result of motion restriction of the endoscope. This spring is fabricated such that the material wire thereof is spirally coiled, and is simultaneously twisted so that forcing pressure is introduced in the spring in the direction in which the adjoining ring portions thereof are brought into pressure contact with one another it is subjected to tension.

12 Claims, 5 Drawing Sheets

TIP ARTICULATION MECHANISM FOR ENDOSCOPES

BACKGROUND AND SUMMARY OF THE INVENTION

The present invention relates to improvements in a tip articulation mechanism for endoscopes.

In general, an endoscope is provided with a proximal grip section, and an inserting portion of a small diameter which extends from this grip section.

The inserting portion is internally fitted with a pulling wire for tip articulation. This wire is fixed in an distal end thereof to an outermost sheathing tube by soldering or any other suitable means, and also, is connected in the base end thereof to an articulation controlling knob of the grip section which can be axially slid for articulating the distal portion of endoscope proximal.

With such arrangement, a sliding operation of the articulation controlling knob towards the base end side thereof allows the distal portion of endoscope to be articulated.

However, when the inserting portion is inserted in an internal bodily organ such as a blood vessel, the operating wire occasionally undergoes an overload owing to physical resistance or other similar factor acting upon the distal portion of endoscope during the articulating operation of the distal portion of endoscope.

If an overload is exerted upon the pulling wire, there is the risk that the pulling wire is broken in the soldered end portion thereof, and/or any excessive operation force of the distal portion of endoscope causes the blood vessel or other internal bodily organ to injure. This is a disadvantage of the generally known conventional tip articulation mechanism for endoscopes.

It is therefore a primary object of the present invention to provide for an improved tip articulation mechanism for endoscopes, which is superior in the durability thereof, and is free from any task of injury of internal bodily organ such as a blood vessel, in which the foregoing disadvantage of the conventional tip articulation mechanism for endoscopes are overcome.

BRIEF DESCRIPTION OF THE DRAWINGS

The present invention will be described with reference to the accompanying drawings, in which.

DETAILED DESCRIPTION OF THE PREFERRED EMBODIMENTS

The preferred embodiments of the tip articulation mechanism according to the present invention will be described in detail with reference to FIGS. 1 to 8.

Figure 1:
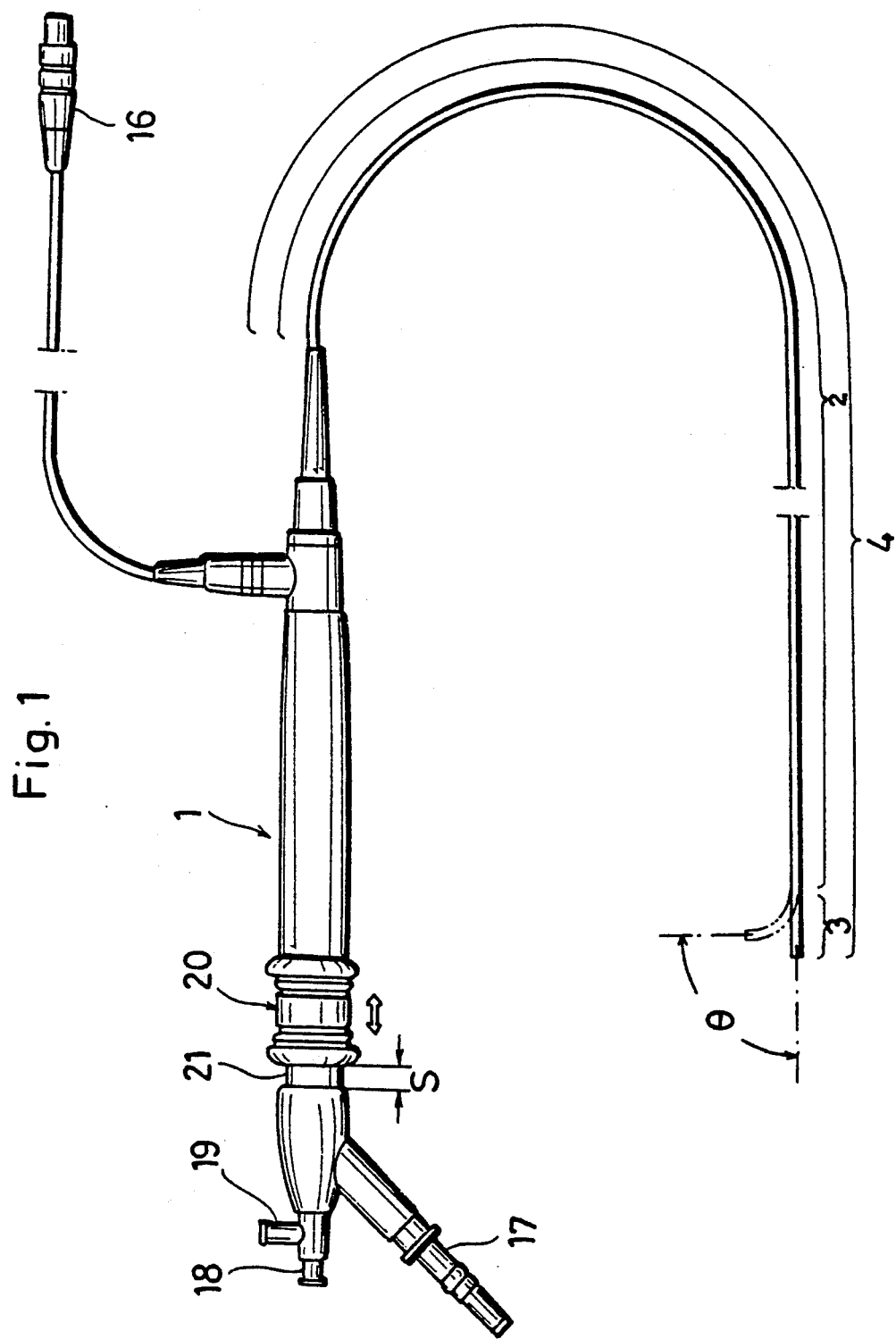
FIG. 1 is an elevational view of an endoscope which includes the tip articulation mechanism of the present invention according to a first preferred embodiment thereof.

FIG. 1 shows a medical endoscope which includes the tip articulation mechanism according to the present invention. This endoscope is provided with a grip section 1 at the base end thereof, and the grip section 1 is fitted with a catheter portion 2 of an extremely small diameter and an articulation tip 3 in the order named.

The catheter, portion 2 is furnished with a suitable degree of flexibility and rigidity against forcing pressure. The articulation tip 3 is straightened or curved as shown with a full line or two-dot chain line in FIG. 1.

The catheter portion 2 and the articulation tip 3 together form an inserting portion 4 of the endoscope. This inserting portion 4 is desired to be 3 mm or below in the outside diameter thereof, and in all of the preferred embodiments, the outside diameter of the inserting portion 4 is set to 2.3 mm.

Figure 2:
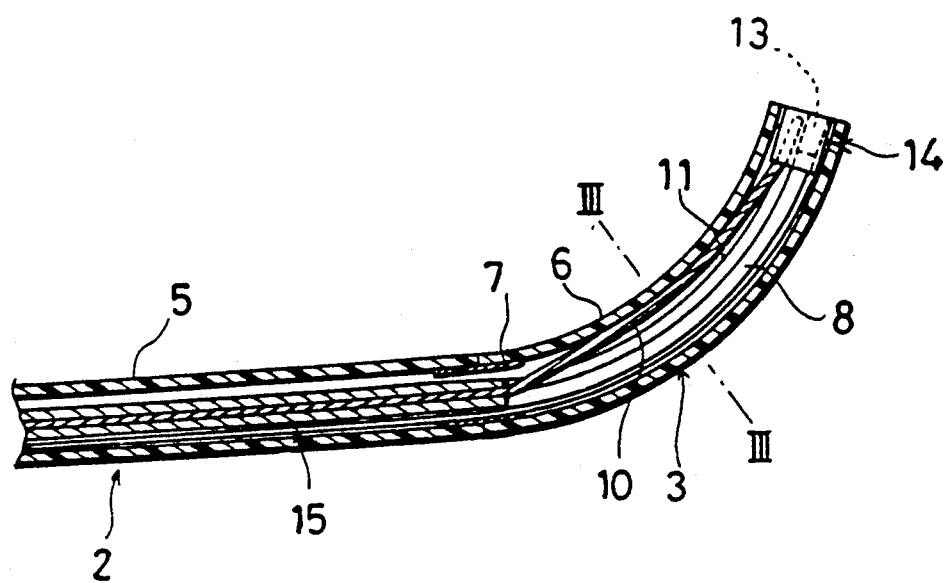
FIG. 2 is an enlarged sectional view of an end of an inserting portion of the endoscope as shown in FIG. 1.

As shown in FIG. 2, the catheter portion 2 which forms a substantial portion of the inserting portion 4 comprises a sheathing tube 5 on the outermost surface thereof. This sheathing tube 5 may be a stainless steel spiral tube in a sectionally flat rectangular configuration which is coated with plastics, or a plastic tube or any other suitable similar tubular, member.

Also, as far as the articulation tip 3 is concerned, the outermost surface thereof comprises a tube 6 made from plastics such as urethane resin or the like.

In FIG. 2, the sheathing tube 5 and the plastic tube are connected by using a connector tube 7 of small length which is made of stainless steel or any other suitable material.

Figure 3:
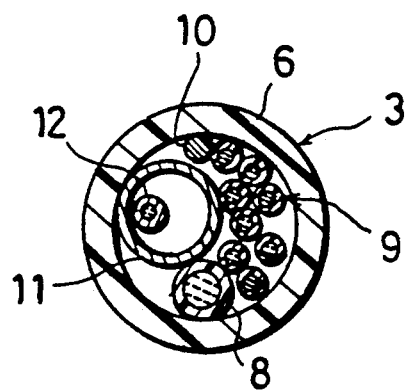
FIG. 3 is an enlarged sectional view taken along the line III—III of FIG. 2.

The sheathing tube 5 and the plastic tube 6 have an image guide 8, a light guide 9, a pulling wire 10, and a working channel 11 inserted into themselves as shown in FIGS. 2 and 3.

The working channel 11 is made from, for example, fluorocarbon resin or any other suitable similar material, and has a laser fiber 12 or the like fitted thereinto from the base end thereof. As applied in the preferred embodiments of the present invention, this working channel 11 may be, for example, 0.83 mm in the inside diameter, thereof and 0.99 mm in the outside diameter thereof, while on the other, hand, the laser fiber may be 0.48 mm in. The outside diameter thereof.

The image guide 8 is fitted with an objective lens 13 such as a rod lens on the tip surface thereof by means of adhesives or the like. The end portion of the image guide 8 and that of the pulling wire 10 such as a stainless steel wire are connected with each other into a single unit relation through an end connecting means 14.

Specifically, the end portion of the objective lens 13 and that of the image guide 8 are inserted into the end connecting means 14, and are fixed therein by using adhesives, while at the same time, the end of the pulling wire 10 and that of the light guide 9 are similarly fixed within the end connecting means 14 by using adhesives. The end connecting means 14 is secured on the inside surface of the end portion of the plastic tube 6 by the use of adhesives.

The pulling wire 10 is slidably inserted through a wire guide pipe 15 made of such as stainless steel, and as is apparent from the preceding description, the end portion of this wire 10 is secured on the end portion of the plastic tube 6 through the end connecting means 14. On the other hand, the end portion of the wire guide pipe 15 is fixed c),-j the end of the sheathing tube 5 by using adhesives or the like.

With such arrangement, if the pulling wire 10 is subjected to tension from the base end side thereof, the pulling wipe 10 is linearized as a bowstring, or is let to approach a linear form as a bowstring, in the range from the end of the wire guide pipe 15 to the end connecting means 14, thereby allowing the articulation tip 3 to be curved as shown in FIG. 2 or with the imaginary line in FIG. 1. If the pulling wire is released from the tension, the articulation tip 3 is restored to the straight form thereof by using the resiliency of the image guide 8 and the like.

The pulling wire 10 is for example 0.2 mm in the outside diameter thereof and such as 760 mm in the length thereof. The inside diameter, the outside diameter and the length of the wire guide pipe 15 are 0.25 mm, 0.35 mm and 620 mm respectively in the preferred embodiments of the present invention. Although the wire guide pipe 15 is employed in FIG. 2, the disuse of this wire guide pipe 15 is feasible if the sheathing tube 5 is great in the rigidity thereof to some extent.

The image guide 8 comprises a glass portion in which a great number of picture elements including cores and cladding are integrated, and a covering layer which mantles the glass portion. The light guide 9 comprises a number of optical fiber element made of plastic or multicomponent glass.

The grip section 1 is separated in the end portion thereof into the inserting portion 4 and a light guide plug 16 as shown in FIG. 1. Moreover, the grip section 1 is ramified in the base end portion thereof into an image guide plug 17 and a connector, means 18 for inserting a laser fiber through the endoscope. An inlet means 19 is used to pour a physiological solution of sodium chloride into the endoscope.

The image guide plug 17 is connected to the head of a camera not shown, to display images of the inner surfaces of the internal bodily organs by using a monitoring CRT, manely, cathode ray tube or other suitable apparatus through an image processing system. Also, the light guide plug 16 is connected to the head of a lamp (not shown) of a light source, and receives light from this lamp, to thereby transmit it to the tip of the inserting portion 4 through the abovementioned light guide 9 so that the light is radiated from this tip, thereby illuminating the watching area of an internal bodily organ into which the endoscope is inserted.

A small cylinder type articulation controlling section 20 is slipped on to a guide portion 21 on the base end side of the grip section 1 so that this operating section can be axially slid to allow it to be axially moved by holding it between the index finger and the second finger.

Figure 4:
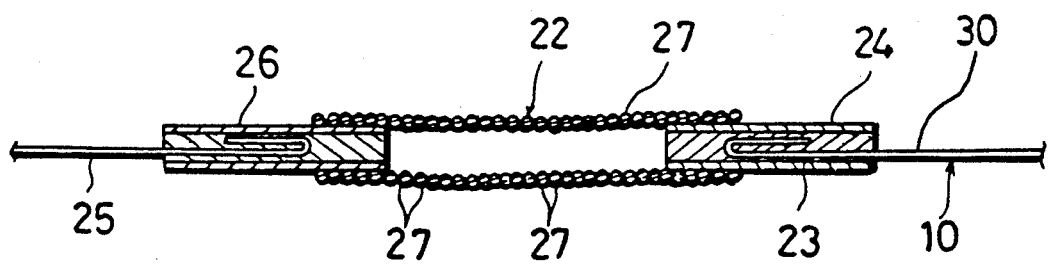
FIG. 4 is an enlarged sectional view of a principal portion of the endoscope as shown in FIG. 1.

In FIG. 4, the pulling wire 10 is fitted with an overload preventing spring 22 in the middle thereof. The location of this spring 22 in the pulling wire 10 may be at any middle position of the wipe 10, as a general rule.

In practice, however,, the wire 10 is located within the grip section 1.

The pulling wire 10 comprises a first segment 30 and a second segment 25. A base grid portion 23 of the fir.,,t segment 30 is inserted in a first tube 24 of a small diameter, and is secured in this first tube 24 by soldering or any other suitable means, while on the other hand, an end portion of the second segment 25 is fitted into a second tube 26 of a small diameter, and is fixed in this second tube 26 by soldering or any other suitable means. The second segment 25 is connected in a base end (not shown) thereof to the articulation controlling section 20. See FIG. 1.

Moreover, the overload preventing spring 22 is connected in both ends thereof to the outer circumferential surface of the first and second tubes of small diameters by soldering or any other suitable means. This spring 22 is twisted so that an internal stress is created therein in the direction in which the adjoining Ping portions thereof are forced into contact with one another.

Figure 5:
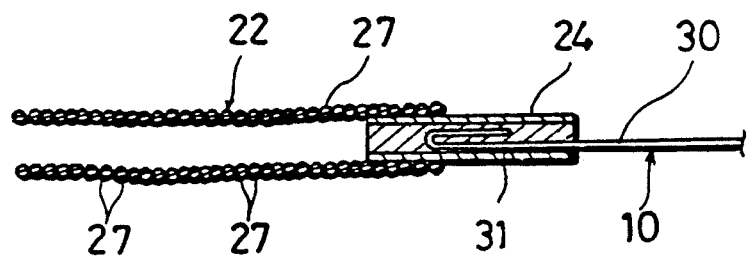
FIG. 5 is an enlarged sectional view of a principal portion of the endoscope which includes the tip articulation mechanism according to a second preferred embodiment of the present invention.

Also, in a second preferred embodiment of the present invention as shown in FIG. 5, the pulling wipe 10 may comprise the first segment 30 alone without the second segment 25 illustrated in FIG. 4. In this case, an end portion 31 of the pulling wire 10 is inserted and secured in the first tube 24 of a small diameter by soldering or any other suitable means. Moreover, the overload preventing spring 22 is fixed in an end thereof to the outer circumferential surface of the first tube 24 of a small diameter by soldering or any other similar means, while at the same, the spring 22 is directly secured in the base end thereof on the outer circumferential surface of the articulation controlling section 20. See FIG. 1.

Alternatively, the second segment 25 of the pulling wire 10 may not be used, and the second tube C-6 of a small diameter may be secured on the articulation controlling section 20.

With such arrangement, if the articulation controlling section 20 is slid in the direction of the base end side thereof (by using the fingers), the pulling wipe 10 is drawn to the base end side thereof, thereby allowing the articulation tip 3 to be articulated as shown in FIG. 2.

Figure 7:
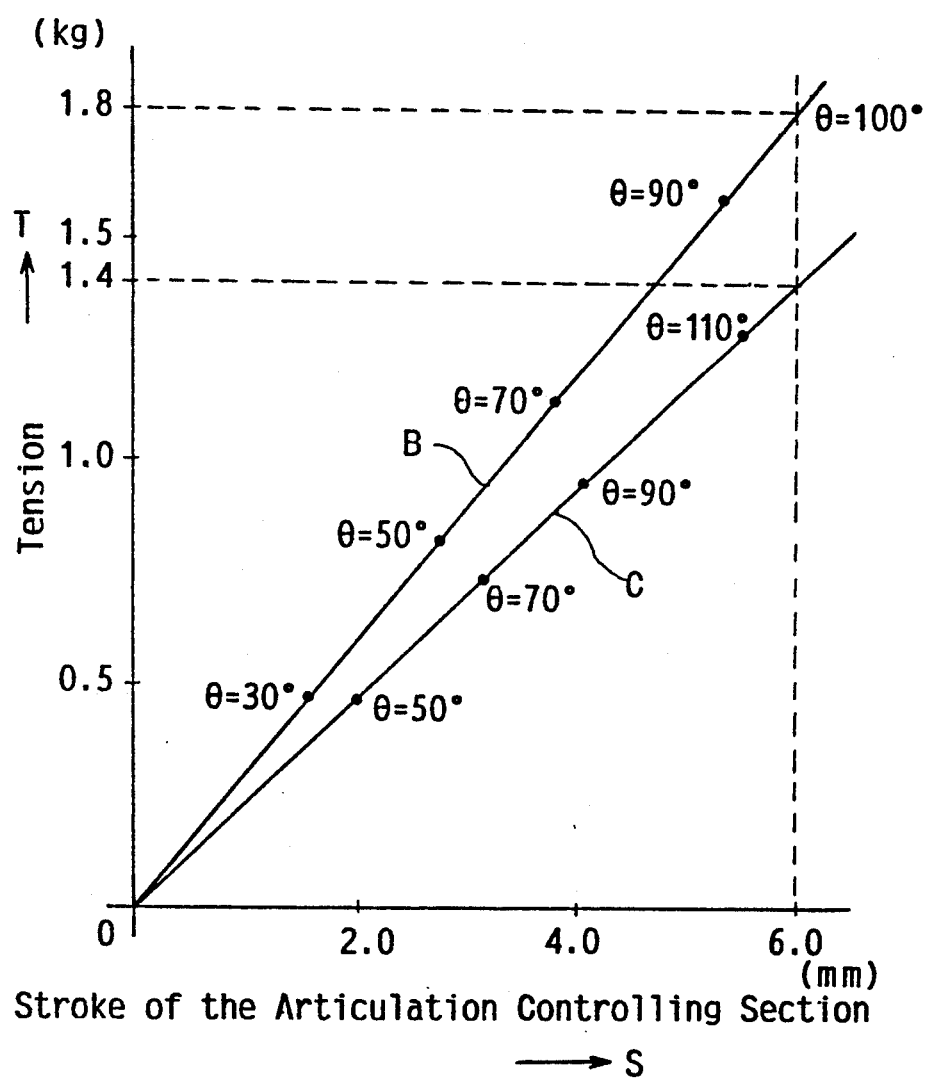
FIG. 7 is a graph which shows the interrelations among the stroke of an articulation controlling section of an endoscope which includes the tip articulation mechanism of the present invention, the tension exerted on the overload preventing wire, and the angles through which the distal portion of endoscope is articulated.

FIG. 7 is a graph which shows the interrelations of the stroke of the articulation controlling section 20, the maximum allowable tension exerted upon the pulling wire 10, and the angle $\theta$ through which the articulation tip 3 is articulated. Their respective values are obtained from their actual measurement. This graph gives the maximum allowable tension Tmax to be exerted upon the over-load preventing spring 22.

In the graph of FIG. 7, the straight line B is for the case in which the articulation tip 3 was articulated while the inserting portion 4 was partially rounded by giving a ½ turn thereto along a circle of 50 mm in the inside diameter thereof, with the laser fiber 12 inserted through the working channel 11.

Also, the straight line C was obtained when the articulation tip 3 was actuated, while the laser fiber, 12 was fitted in the working channel 11, with the inserting portion 4 straightened.

Therefore, when the stroke of the articulation controlling section 20 is 6 mm, the maximum value thereof, the maximum allowable tension upon the overload preventing spring 22 is 1.4 kg in the case of the straight line C, and 1.8 kg in the straight line B.

The overload preventing spring 22 is desired to be high in the initial tension Fo (kg) thereof, and small in the spring constant K (kg/mm) thereof, and is also required to satisfy the following formulas for the relations between the initial tension Fo and the maximum allowable tension and between the spring constant and the maximum allowable tension.

$$\tfrac{1}{2} \times Tmax \leqq Fo \leqq 1.5 \times Tmax$$

$$1/20 \times Tmax \leqq K \leqq \tfrac{1}{2} \times Tmax$$

The initial tension Fo is a value of tension which causes the spring 22 to begin stretching over the overall length thereof.

Figure 6:
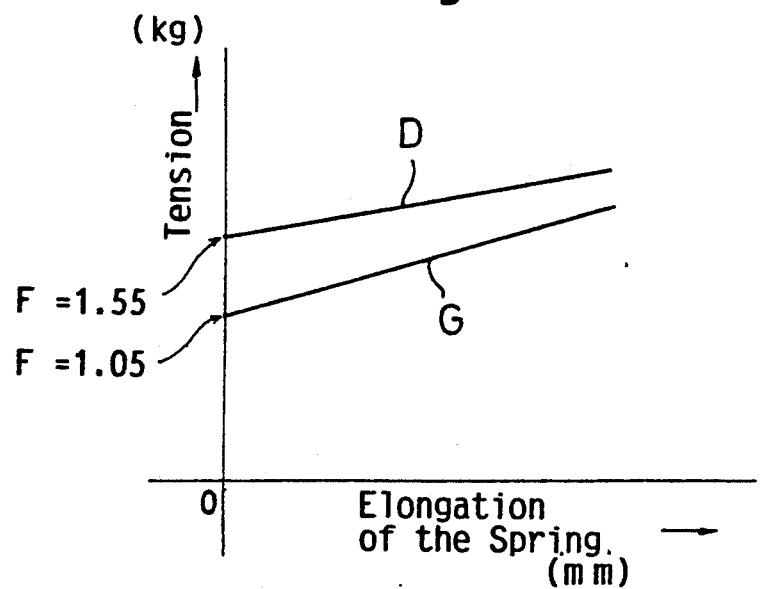
FIG. 6 is a graph which shows the characteristics of an overload preventing spring attached to the middle of a pulling wire applied to an endoscope which includes the tip articulation mechanism of the present invention.

Also, the tension resistivity of the pulling wire 10 is set to approximately four times the maximum allowable tension Tmax. In practice, an applicable overload preventing spring 22 is as specified in the graph of the spring characteristics of FIG. 6. That is to say, the spring D in FIG. 6 is 1.55 kg in the initial tension Fo thereof and 0.17 kg/mm in the spring contact K thereof. Also, the spring 6 in the same figure is 1.05 kg in the initial tension Fo thereof and 0.23 kg/mm in the spring constant K thereof. If the spring D, for instance is applied to the overload preventing spring 22, it does not stretch in the entirety thereof until it is subjected to tension T (kg) which exceeds the specified initial tension thereof, 1.55 kg. If more than the initial tension of 1.55 kg is exerted upon this overload preventing spring 22, this spring stretches in the proportion of (T−Fo)/K.

Thus, a spring which is high in the initial tension Fo thereof and low in the spring constant thereof as compared with conventional tension springs is particularly selected as the overload preventing spring 22.

Therefore, if the pulling wire 10 is subjected to an overload (tension T exceeding the maximum allowable tension Tmax) which can be caused by physical resistance acting thereupon when the distal portion of endoscope is articulated, any excessive tension which results in the overload can be absorbed in elongation of the overload preventing spring 22. This obviates damage or any other similar trouble of the pulling wire 10 and injury of the blood vessels or the like into which the inserting portion 4 is inserted. (If the tip articulation mechanism according to the present invention is subjected to smaller tension than the maximum allowable tension Tmax, said mechanism operates without the use of the function of the overload preventing spring 22.)

The overload preventing spring 22 is made of, for example, a piano wire. In fabrication, this piano wire is spirally coiled, and is simultaneously twisted so that forcing pressure is created in the direction in which the adjoining ring portions 27, 27 of the wipe are brought into pressure contact with one another when the wire is subjected to tension.

Also, this wire of which the spring 22 is made is annealed at a low temperature of 180° C. to 250° C.

In operation, if the overload preventing spring 22 has tension T applied thereto, this tension T is expended to untwist the ring portions 27 unless the tension T exceeds the specified initial tension Fo. If the tension applied to the overload preventing spring 22 becomes greater than the initial tension Fo, the tension is used to space the adjoining ring portions 27 apart which have kept in close contact with one another, so that the overload preventing spring 22 stretches as a whole.

Also, in the endoscope which includes the tip articulation mechanism according to the present invention, the maximum stroke S of the articulation controlling section 20 is desired to be limited to 10 mm so that the articulation tip 3 is not articulated through 150 degrees or above to prevent any damage thereof when the inserting portion 4 is not inserted through a model of a blood vessel or other internal bodily organ, and also, is straightened, while at the same time, the working channel 11 has not the laser fiber 12 fitted thereinto.

Therefore, according to the tip articulation mechanism constructed as described in the foregoing, as long as this mechanism is subjected to a smaller tension than the specified initial tension Fo, the articulation tip 3 is articulated under the substantially same condition as when the articulation tip 3 is not provided with the overload preventing spring 22. However, even if the tension exerted upon the mechanism of the present invention exceeds the specified initial tension Fo, the articulating motion of the articulation tip 3 is suddenly mitigated so that the articulation tip 3 is not curved through 150 degrees or more.

The following Table 1 shows the results of an articulating test, which include the angles through which the articulation tip 3 was repeatedly articulated by operating the articulation controlling section 20 to the maximum allowable stroke.

TABLE 1

| TESTING CONDITIONS | | | Cumulative | |
| --- | --- | --- | --- | --- |
| State of the Inserting Portion | Insertion of the Laser Fiber | Insertion into a Model of an internal Bodily Organ | Frequency of Articulation of Endoscope Tip (times) | Angle of Articulation θ (deg.) |
| Straight | No | No | 1 | 130 |
| Straight | Yes | No | 100 | 100 |
| | | | 500 | 100 |
| | | | 1000 | 100 |
| Straight | Yes | Yes | 1100 | 98 |
| | | | 1400 | 98 |
| | | | 1700 | 98 |
| | | | 2000 | 98 |
| ¼ Round of φ 50 mm Circle | Yes | Yes | 2100 | 80 |
| | | | 2500 | 80 |
| | | | 3000 | 80 |
| ½ Round of φ 50 mm Circle | Yes | Yes | 3100 | 70 |
| | | | 3500 | 70 |
| | | | 4000 | 70 |
| 1 Round of φ 50 mm Circle | Yes | Yes | 4100 | 50 |
| | | | 4500 | 50 |
| | | | 5000 | 50 |
| Straight | Yes | Yes | 5001 | 100 |
| Straight | No | No | 5002 | 130 |

In Table 1 the column titled "State of the Inserting Portion" has thereunder the expressions "Straight" and "¼ Round of φ50 mm Circle". The former, expression indicates that the inserting portion 4 keeps straightened, and the latter denotes that the inserting portion 4 is partially rounded by giving a ¼ turn thereto along a circle of 50 mm in the diameter thereof.

Similarly, the phrases "½ Round of φ50 mm Circle" and "1 Round of φ50 mm Circle" respectively denote that the inserting portion 4 is partially rounded by giving a ½ turn thereto along a circle of 50 mm in the diameter, thereof, and that the inserting portion 4 is partially given a single turn along a circle of 50 mm in the diameter thereof.

Also, the expressions "Yes" and "No" under, the column titled "Insertion of the Laser Fiber" respectively designate that the laser fiber 12 is inserted in the working channel 11 and that the laser, fiber 12 is not inserted in the working channel 11. The words "Yes"

and "No" in the column titled "Insertion in a Model of an Internal Bodily Organ" respectively indicate that the inserting portion 4 is inserted in a model of an internal bodily organ such as a blood vessel and that such insertion of the inserting portion 4 is not conducted.

As is apparent from Table 1, the first testing is performed, with the inserting portion straightened and without inserting the laser fiber and the inserting portion respectively into the working channel and a model of an internal bodily organ. In the second to the thousandth testing, the testing is performed under the same conditions as in the first testing with the exception that the laser fiber is inserted in the working channel, and the angle θ through which the articulation tip 3 is articulated is indicated in Table 1 on the 100th, the 500th and the 1000th testing. In the 1001st to the 2000th testing, the inserting portion 4 is inserted in the internal bodily organ model, and the laser fiber 12 is fitted into the working channel 11. The angle θ through which the articulation tip 3 is articulated is shown in Table 1 on the 1100th, the 1400th, the 1700th and the 2000th testing.

In the 2001st to the 3000th testing, the inserting portion 4 is partially rounded by giving a ¼ turn thereto along a circle of 50 mm in the diameter, thereof, and also, the laser fiber is inserted in the working channel. On the 2100th, the 2500th and the 3000th testing, the angle θ through which the articulation tip 3 is articulated is indicated in Table 1.

As shown also in Table 1, in the 3001st to 4000th testing, the inserting portion 4 is partially rounded by giving a ½ turn along a circle of 50 mm in the diameter thereof, and also, the laser fiber is inserted in the working channel. In these testings, the angle θ through which the articulation tip 3 is articulated is shown on the 3100th, the 3500th and the 4000th testing.

In the 4001st to the 5000th testing, the inserting portion 4 is partially rounded by giving a whole single turn thereto along a circle of 50 mm in the diameter thereof, and the laser fiber 12 is inserted in the working channel 11, with the inserting portion 4 fitted in the model blood vessel. As is apparent from the foregoing, the testing conditions are changed to more severe conditions at intervals of 1000 times of the testing.

Also, in the 5001st testing, a measurement is taken of the angle θ through which the articulation tip 3 is articulated under the same conditions as in the 2nd to the 1000th testing, in which the inserting portion 4 keeps straightened, and the laser, fiber, is fitted in the working channel without fitting the inserting portion in the model blood vessel. Moreover, the 5002nd testing is conducted under the same conditions as in the first testing, in which the inserting portion 4 remains straightened, and the laser fiber is not inserted in the working channel without fitting the inserting portion into the model blood vessel.

As is apparent from Table 1, even if the articulation tip is articulated under the same conditions as in the 1st, to 1000th testing after the 5000th testing has been finished, the articulating angle of the articulation tip remains unreduced, and this demonstrates that the articulation tip does not deteriorate in the articulating performance thereof.

In the foregoing testings, the articulation tip 3 is subjected to more frequent articulating operations of 4000 to 5000 times in cumulative frequency than the general actual service conditions. Therefore, the articulation mechanism according to the present invention provides for endoscopes which are free from any breakage thereof under more severe service conditions, and achieve the prevention of unexpected abnormal breakage thereof and improvement in their service life over a long period of time.

On the other hand, 50% and 90% of endoscopes which include the conventional tip articulation mechanism are respectively broken in the 1000 times of articulating and 3000 times of articulating in cumulative frequency.

Figure 8:
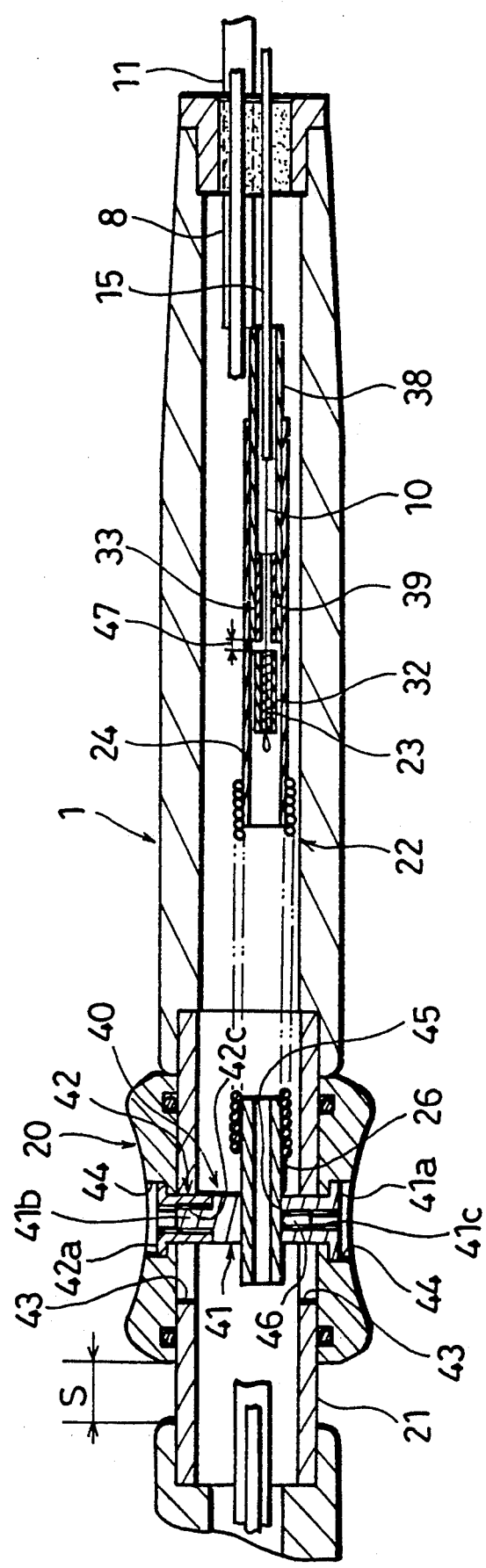
FIG. 8 is an enlarged sectional view of the tip articulation mechanism of the present invention according to a third preferred embodiment thereof.

Next, a second preferred embodiment of the tip articulation mechanism according to the present invention is now described with reference to FIG. 8 which is an enlarged view of a principal portion thereof. In FIG. 8, the base end 23 of the pulling wire 10 is provided with a holding portion 32, and this holding portion 32 is inserted in the first small-diameter tube 24. The first small-diameter tube 24 has an insertion tube 38 fitted therein such that this insertion tube 38 juts in an end portion thereof from the first small-diameter tube 24, while on the other hand, the insertion tube 38 has a small cylindrical body 39 inserted in the base end portion thereof. The first small-diameter tube 24 and the insertion tube 38 are integrated into a single unit relation by soldering or by using adhesives or the like, and the insertion tube 38 and the cylindrical body 39 are also joined with each other into a single unit relation by soldering or by means of adhesives or the like.

Also, the holding portion 32 comprises a sleeve member which is slipped on to the base end of the pulling wire 10, and this sleeve member is secured to the pulling wire 10 by soldering or by using any other suitable means.

The second small-diameter tube 26 connected to the base end of the overload preventing spring 22 is held by means of a supporter means 40 provided in the articulation controlling section 20. This supporter means 40 is also used to hold the second small-diameter tube 26 on the articulation controlling section 20.

In construction, the supporter means 40 is provided with a first supporter segment 41 and a second supporter segment 42 which is engaged with a male-threaded portion 41b of said first supporter segment.

Specifically, the guide portion 21 is provided with through-holes 43, 43 in the circumferential wall of a cylindrical body thereof, and also, the articulation controlling section 20 is formed with through-holes 44, 44 in the circumferential wall thereof. The first supporter segment 41 is inserted in one through-hole 43 of the guide portion via one through-hole 44 of the articulation controlling section, while on the other hand, the second supporter segment 42 is inserted in the other through-hole 43 via the other through-hole 44, and simultaneously, the male-threaded portion 41b of the first supporter segment 41 is engaged with a tapped hole 42C of the second supporter segment 42. In this case, a flange portion 41a of the first supporter segment 41 is mated with a raised portion of said one through-hole 44, while at the same time, a flange portion 42a of the second supporter segment 42 is engaged with a raised portion of said other through-hole 44.

This arrangement achieves the integration of the articulation controlling section 20 and the supporter means 40 into a single unit, and an axial sliding operation of the articulation controlling section 20 allows the supporter means 40 to be axially slid. Tile axial stroke S of the articulation controlling section 20 is such that the supporter means 40 can travel within the limits of the through-hole 43, 43 of the guide portion 21.

The first supporter segment 41 of the supporter means 40 is provided with a holed portion 45, and this holed portion 45 has the second small-diameter tube 26 inserted therein. The first supporter segment 41 is also formed with a tapped hole 41C, and this tapped hole 41C has a screw engaged therewith, to thereby hold the second small-diameter tube 26 in the supporter means 40.

With such arrangement, in a free state of the tip articulation mechanism according to the second preferred embodiment of the present invention, in which the articulation controlling section 20 is located at the furtherest end of the guide portion 21, and is free from any tension in the direction of the base end side of the guide portion 21, a spacing 47 is created between the base end side holding portion 32 of the pulling wire 10 and an engaging protruding portion 33 formed by means of the small cylindrical body 39.

The wire guide pipe 15 is fixed on the end portion of the grip section 1 by using adhesives or the like.

Therefore, in the tip articulation mechanism according to the foregoing second preferred embodiment of the present invention, if the articulation controlling section 20 is slid in the direction of the base end thereof from a free state thereof as illustrated in FIG. 8 in which the articulation tip 3 is straightened, the first small-diameter tube 24 is moved towards the base end side thereof, and if the spacing 47 is reduced to zero, the engaging protruding portion 33 is brought into contact with the base end side holding portion 32 of the pulling wire 10. If the articulation controlling section 20 is additionally slid towards the base end thereof, the pulling wire is drawn to the base end thereof, to thereby allow an articulating operation of the articulation tip.

In this case, if the tension applied to the pulling wire 10 is smaller than the specified initial tension Fo, an articulating operation of the articulation tip 3 (not shown in FIG. 8) is performed under the same condition as when the overload preventing spring is not provided. Also, if the pulling wire 10 is subjected to tension which exceeds the initial tension Fo, the overload preventing spring operates, and as a result, the articulation tip 3 is suddenly reduced in the motion thereof so that the articulation tip 3 is not curved. These are as also described with respect to the first preferred embodiment of the present invention.

Moreover, since the spacing 47, namely, a play is made between the holding portion 32 at the base end of the pulling wire 10 and the engaging protruding portion 33 in a free state of the tip articulation mechanism according to the second preferred embodiment of the present invention, a slight amount of sliding operation of the articulation controlling section 20 does not result in any articulating operation of the articulation tip. That is to say, the foregoing play allows an easy operation of the articulation controlling section 20.

According to the tip articulation mechanism of the present invention, the overload preventing spring 22 is used to absorb any excessive tension which is exerted upon the pulling wire 10 owing to physical resistance or any other similar factor acting upon the articulation tip 3, thereby obtaining unexampled great effects upon the damage prevention of endoscopes which include the tip articulation mechanism of the present invention, and upon the protection of internal bodily organs against any injury.

Moreover, the tip articulation mechanism of the present invention improves the durability of any endoscopes constructed such as to include said mechanism, and allows them to display the constant articulating performance of their articulation tip even if it is repeatably operated.

Although the present invention has been fully described by way of examples with reference to the accompanying drawings, it is to be noted here that various changes and modifications will be apparent to those skilled in the art. Therefore, unless otherwise such changes and modifications depart from the scope of the present invention, they should be construed as being included therein.

We claim:

1. A tip articulation mechanism for endoscopes, comprising:
 a pulling wire having first and second base end portions; and
 an overload preventing spring having first and second axial end portions, wherein said first and second axial end portions of said overload preventing spring are respectively connected to said first and second base end portions of said pulling wire so as to locate said spring between said base end portions of said pulling wire, and wherein said spring is arranged to begin stretching if said spring is subjected to more than a certain amount of tension.

2. A tip articulation mechanism for endoscopes, as set forth in claim 1, wherein a grip section located at the base end portion of an endoscope is provided with an articulation controlling section adapted to slide axially, while at the same time, the pulling wire is connected in the base end thereof to said articulation controlling section.

3. A tip articulation mechanism for endoscopes, comprising:
 a pulling wire having at least one base end portion; and
 an overload preventing spring having first and second axial end portions, wherein one of said axial end portions of said spring is connected to said base end portion of said pulling wire, and wherein said spring is arranged to begin stretching if said spring is subjected to more than a certain amount of tension.

4. A tip articulation mechanism for endoscopes, as set forth in claim 3, wherein the grip section located at the base end portion of an endoscope is provided with an articulation controlling section adapted to slide axially, while at the same time, the base end of the overload preventing spring is connected to said articulation controlling section.

5. A tip articulation mechanism for endoscopes, comprising:
 a grip section located at a base end portion of an endoscope having an engaging protruding portion with which a base end side holding portion of a pulling wire is engaged as a result of a movement of an articulation controlling section towards the base end side of said controlling section to draw the pulling wire in the direction of the base end side of said wire; and
 an overload preventing spring having first and second axial end portions, said first axial end portion being connected to said engaging protruding portion and said second axial end portion being connected to the articulation controlling section, wherein a spacing is provided between the base end side holding portion of the pulling wire and the engaging protruding portion in a free state of said wire.

6. A tip articulation mechanism for endoscopes, as set forth in claim 1, 3 or 5, wherein the overload preventing spring is fabricated such that the material wire thereof is spirally coiled, and is simultaneously twisted so that forcing pressure is introduced therein in the direction in which the adjoining ring portions of said spring are brought into pressure contact with one another when said spring is subjected to tension.

7. A tip articulation mechanism for endoscopes, as set forth in claim 1, 3 or 5, wherein the overload preventing spring satisfies the formula $\frac{1}{2} \times Tmax \leq Fo \leq 1.5 \times Tmax$ for the relation between the initial tension Fo which causes said spring to begin displacement thereof, and the maximum allowable working tension Tmax.

8. A tip articulation mechanism for endoscopes, as set forth in claim 1, 3 or 5, wherein the overload preventing spring satisfies the formula $1/20 \times Tmax \leq K \leq \frac{1}{2} \times Tmax$ for the relation between the spring constant K and the maximum allowable working tension Tmax.

9. A tip articulation mechanism for endoscopes, as set forth in claim 1, 3 or 5, wherein the base end portion of the pulling wire has the maximum stroke of 10 mm.

10. A tip articulation mechanism for endoscopes, as set forth in claim 1, 3 or 5, wherein the tension resistivity of the pulling wire is approximately four times the maximum allowable tension of the overload preventing spring.

11. A tip articulation mechanism for endoscopes, as set forth in claim 6, wherein the overload preventing spring is made of a piano wire.

12. A tip articulation mechanism for endoscopes, as set forth in claim 6, wherein the material wire of which the overload preventing spring is made is annealed at a low temperature.

* * * * *